United States Patent
Kado et al.

Patent Number: 5,905,807
Date of Patent: May 18, 1999

[54] APPARATUS FOR EXTRACTING FEATURE POINTS FROM A FACIAL IMAGE

[75] Inventors: Yoshiyasu Kado, Kadoma; Masamichi Nakagawa, Hirakata; Fumio Maehara, Moriguchi, all of Japan

[73] Assignee: Matsushita Electric Industrial Co., Ltd., Kadoma, Japan

[21] Appl. No.: 08/708,873

[22] Filed: Sep. 5, 1996

Related U.S. Application Data

[63] Continuation of application No. 08/229,112, Apr. 18, 1994, abandoned, which is a continuation of application No. 08/006,314, Jan. 22, 1993, abandoned.

[30] Foreign Application Priority Data

Jan. 23, 1992 [JP] Japan ................... 4-009753

[51] Int. Cl.$^6$ ................... G06K 9/46
[52] U.S. Cl. ................... 382/118; 382/199
[58] Field of Search ................... 382/118, 115, 382/190, 195, 197, 199, 261, 270

[56] References Cited

U.S. PATENT DOCUMENTS

| | | | |
|---|---|---|---|
| 3,648,240 | 3/1972 | Jacoby et al. | 382/2 |
| 3,805,238 | 4/1974 | Rothfjell | 382/2 |
| 4,055,833 | 10/1977 | Rothfjell | 382/2 |
| 4,699,149 | 10/1987 | Rice | 382/2 |
| 4,724,542 | 2/1988 | Williford | 382/3 |
| 4,805,223 | 2/1989 | Denyer | 382/127 |
| 4,975,969 | 12/1990 | Tal | 382/116 |
| 4,993,068 | 2/1991 | Piosenka et al. | 382/2 |
| 5,008,946 | 4/1991 | Ando | 382/23 |
| 5,012,522 | 4/1991 | Lambert | 382/2 |
| 5,163,094 | 11/1992 | Prokoski et al. | 382/1 |
| 5,164,992 | 11/1992 | Turk et al. | 382/2 |
| 5,210,797 | 5/1993 | Usui et al. | 382/4 |
| 5,231,674 | 7/1993 | Cleveland et al. | 382/22 |

OTHER PUBLICATIONS

English Abstract of JP 61–208185 dated Sep. 1986.
English Abstract of JP 63–223974 dated Sep. 1988.
Ballard et al "Computer Vision" 1987, pp. 94–111.
Gonzales et al, Digital Image Processing, 1992, pp. 413, 414, and 419.
Alattar, A.M. et al., "Primitive–Based Image Coding Technique For Still Pictures", Proceedings of the 1989 IEEE International Symposium on Circuits and Systems, Cat. No. 89CH2692–2, vol. 2, May 11 1989, Portland, Oregon pp. 1362–1365.
Russ, J.C., "Direction Information from the Sobel Operator", Journal of Computer–Assisted Microscopy, vol. 2, No. 4, Dec. 1990, pp. 239–247.
Buhr, R., "Front Face Analysis and Classification (Analysis und Klassification von Gesichtsbildern)", NTZ Archiv, vol. 8, No. 9, Oct. 1986, pp. 245–255.

*Primary Examiner*—Amelia Au
*Assistant Examiner*—Larry J. Prikockis
*Attorney, Agent, or Firm*—Pillsbury Madison & Sutro LLP

[57] ABSTRACT

A facial image picture data is processed by an edge extraction part, which performs edge extraction on the inputted image picture. The processed data is then converted by a binary level conversion part for each preestimated point of facial elements. An image picture arithmetic processing part performs time-to-time arithmetic computation of correlation values between the data of the binary-leveled edged-image picture and the data having been previously stored in the shape data-base part, and issues an output including extracted data of feature points of the facial image picture.

13 Claims, 11 Drawing Sheets

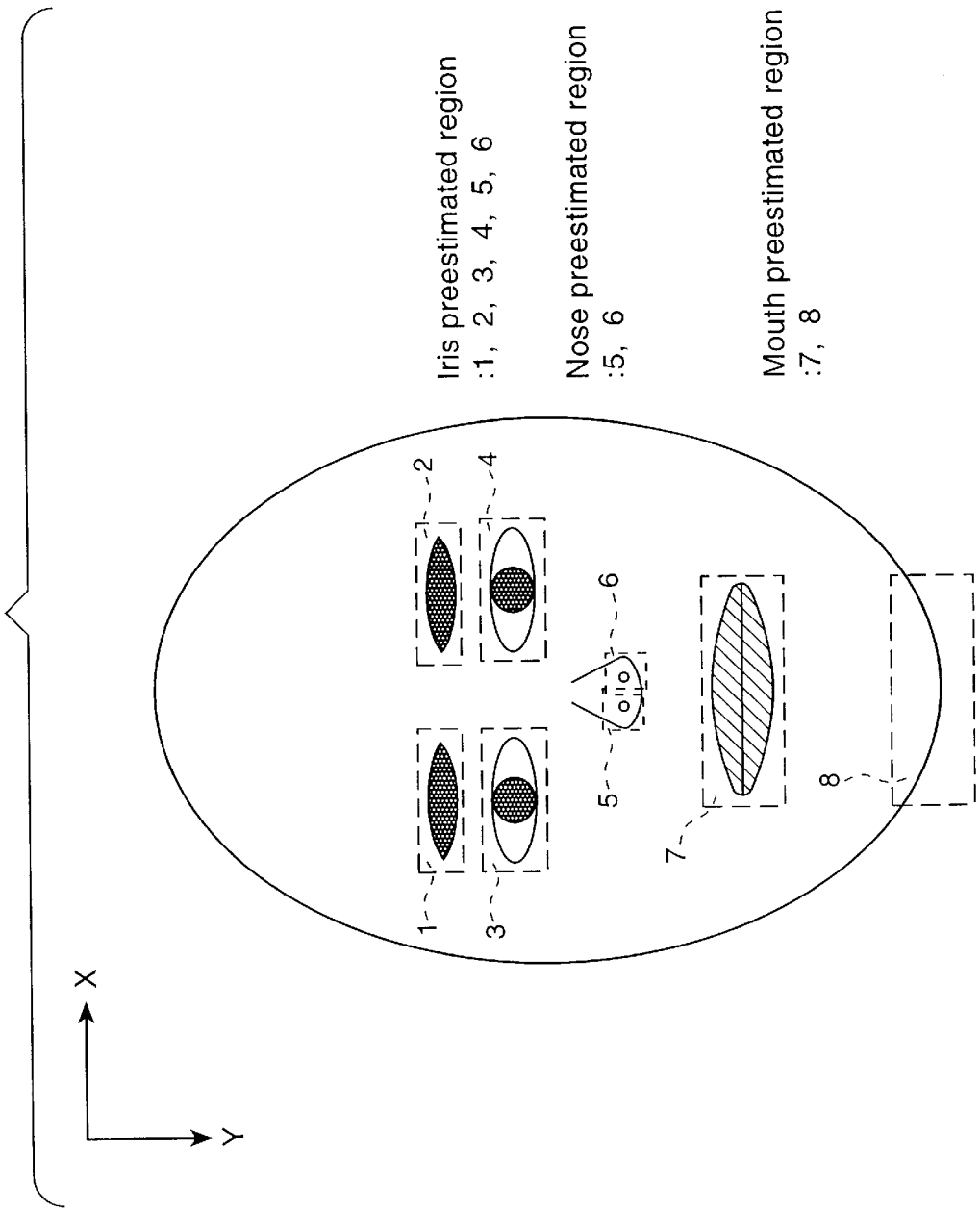

FIG. 3

| Position number k | lk | mk | Vx | Vy |
|---|---|---|---|---|
| 1 | 6 | 12 | 0 | −1 |
| 2 | 9 | 11 | −0.5 | −0.8661 |
| 3 | 11 | 9 | −0.8661 | −0.5 |
| 4 | 12 | 6 | −1 | 0 |
| 5 | 11 | 3 | −0.8661 | 0.5 |
| 6 | 9 | 1 | −0.5 | 0.8661 |
| 7 | 6 | 0 | 0 | 1 |
| 8 | 3 | 1 | 0.5 | 0.8661 |
| 9 | 1 | 3 | 0.8661 | 0.5 |
| 10 | 0 | 6 | 1 | 0 |
| 11 | 1 | 9 | 0.8661 | 0.5 |
| 12 | 3 | 11 | 0.5 | 0.8661 |

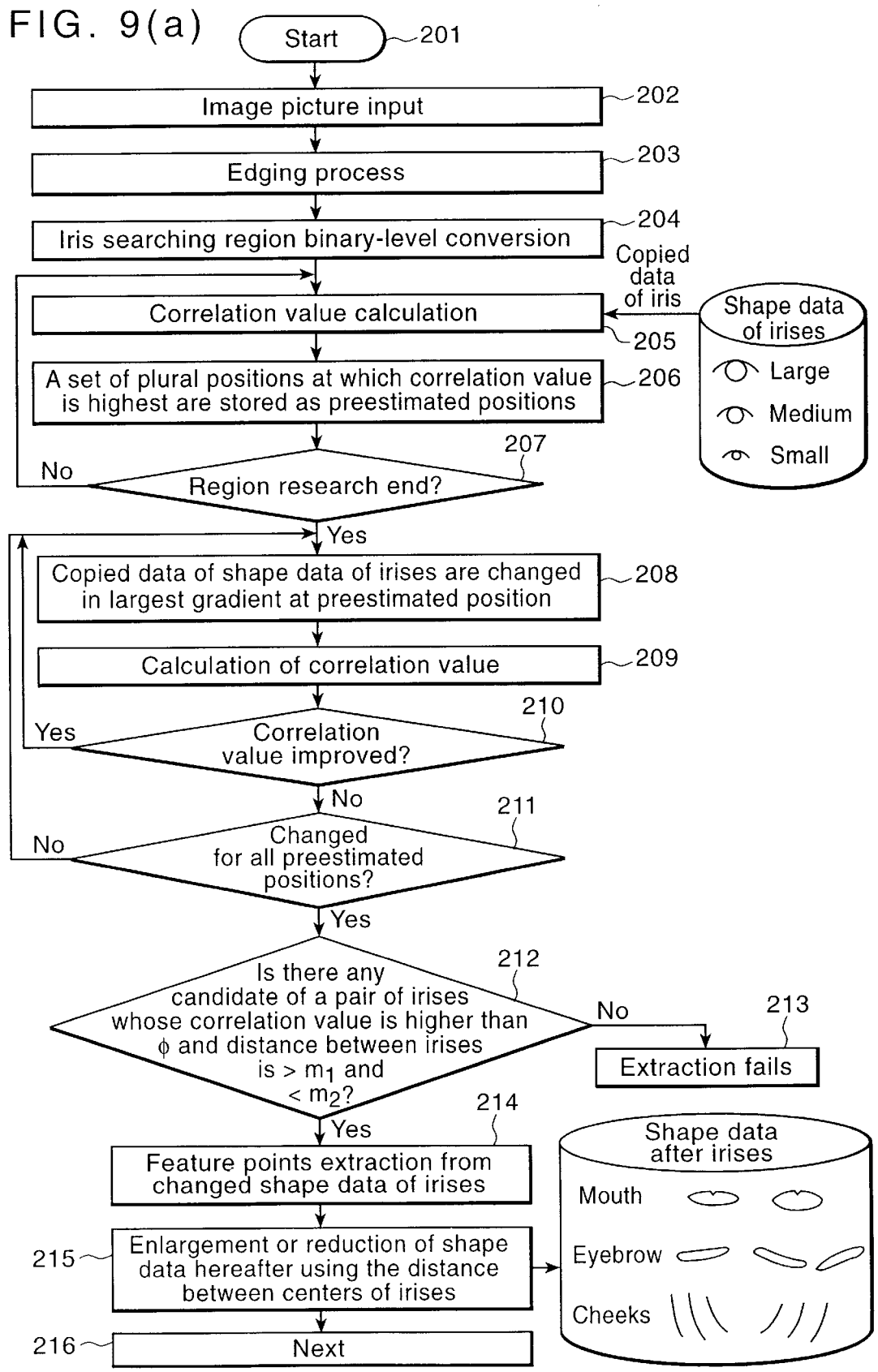

APPARATUS FOR EXTRACTING FEATURE POINTS FROM A FACIAL IMAGE

This a continuation os application Ser. No. 08/229,112, filed on Apr. 18, 1994, which was abandoned upon the filing hereof which is a continuation of application Ser. No. 08/006,314 filed Jan. 22, 1993, now abandoned.

FIELD OF THE INVENTION AND RELATED ART STATEMENT

1. Field of the Invention

The present invention relates to an apparatus for obtaining feature points from an image of a face of an individual in order to recognize facial features.

2. Description of the Related Art

Japanese unexamined Patent Publication (Tokkai) Sho-61-208185 (208185/1986) ("the '185 document") and Japanese unexamined Patent Publication (Tokkai) Sho-63-223974 (223974/1988) ("the '974 document") teach ways of extracting feature points of a facial image picture. The '185 reference teaches that a facial image picture input from an image picture input part is stored in an image picture memory part, and is then is digitized by a binary level conversion part with an appropriate threshold value θ. Values indicative of the characteristic regions of a human face are extracted using characteristic parameters (e.g., area, circumferential length, coordinate of the center of gravity, etc.) from this binary-leveled image picture. The '974 reference teaches that tint conversion is applied to a facial image picture stored in an image picture memory part. Then the region having skin-color is taken as a mask pattern from which the characteristic regions are extracted.

In the above-mentioned prior art, when a binary-leveled image picture is used, and the threshold value θ varies, the areas of obtained characteristic regions also vary. Hence, this prior art has a drawback such that the feature points exhibit deviations depending upon the threshold value θ. Moreover, even for the same face, when the position of the source of light differs at different times of inputting the image picture, the brightness distribution of the facial image also differs. Hence, when conventional binary level conversion is done with a certain fixed threshold value of θ, areas of the characteristic regions of the facial image change. As a result different extraction results would be obtained for the same face under different lighting conditions.

Using the hue has the same problem as described above. Depending on the type of lighting sources, such as sun light, a fluorescent lamp and others, the hue of respective regions, including the skin-color regions, change. Because of these problems the prior art required that the position of lighting, colors, etc. remain constant.

When the hue information is used, and a television camera is used as the image picture input part, the hue information becomes unstable in regions including sharp edges when performing A/D-conversion and storing the input signal into an image picture memory part. This makes an accurate extraction of the feature points of a face impossible.

OBJECT AND SKY OF THE INVENTION

The purpose of the invention is to produce feature points data (data of feature points, i.e. sets of (x, y) value) of the face. The feature points data is used, for example, in a simulation picture composing machine, which produces a picture of a baby, expected by a couple, by processing the feature points data of pictures of the couple.

According to the present invention, in order to solve the above-mentioned problem, the feature points of a face (e.g., an iris, a mouth, a nose, an eyebrow, and a cheek) are extracted using an image picture from which edges are extracted. This is a relatively stable way to extract the position of a facial element even when the lighting conditions vary. However, the lighting conditions will effect the size and shape of an extracted image. The apparatus of the present invention has an edge extraction part and a binary level conversion part for removing noise from the extracted edges of the image picture. Shapes of facial elements, such as a mouth, an eyebrow etc. are stored in a shape data-base part. The shape data copied and a shape data changing part changes copied data of the shape data in order to incorporate differences in the appearance of facial features of the same person's face from time to time, and to match the shape data with the input facial image picture.

In the present invention, for the facial image picture input from an image picture input part, the edges of a facial image picture are extracted by the edge extraction part. The extracted edges of the facial image picture include a large amount of minute noise due to features such as a moustache or skin wrinkles. Therefore, for a searching region, i.e., a region where a facial element (e.g., a pair of eyes) certainly exists (i.e. an eye region, a nose region, a mouth region, etc.), the above-mentioned extracted edges thus obtained by the edge extraction part are converted into binary-leveled extracted edges by a binary level conversion part. From the searching regions of the obtained binary-leveled edged image picture, a region that is close to the shape data stored in a shape data-base part is selected based on the magnitude of its correlation value obtained by an image picture arithmetic processing part. The shape data are changed by a shape data updating part in a manner such that the correlation value is large in the vicinity of the selected region changing. Then, when the correlation value output from the image picture arithmetic processing part reaches at least a certain value, based on the changed shape data, the feature points of a facial element that are the object of the search are output from the output part. That is, in the present invention, when the correlation value reaches at least a certain value, matching for some elements of the face, e.g., an iris, is successful, with regard to the comparison of the data based on an image picture with the data of the shape data base.

The apparatus of the present invention, owing in part to the binary level conversion of the extracted edges of the facial image picture, is robust against variations in the conditions for taking pictures, such as the position or types of lighting sources, skin color, etc. Furthermore, owing to the inclusion of the shape data changing part in the apparatus, personal changes in individual's facial features can be incorporated and absorbed, enabling an improvement in the capability of the extraction of the feature points of a face.

While the novel features of the invention are set forth particularly in the appended claims, the invention, both as to organization and content, will be better understood and appreciated, along with other objects and features thereof, from the following detailed description taken in conjunction with the drawings.

BRIEF DESCRIPTION OF THE DRAWINGS

FIG. 2A shows an example of preestimated regions.

FIG. 3 shows an example of the shape data in the shape data-base part.

FIG. 9(a) and FIG. 9(b), in combination, show a flow chart for an example of the procedure of extraction of the feature points of a facial image, according to the present invention.

It will be recognized that some or all of the Figures are schematic representations for purposes of illustration and do not necessarily depict the actual relative sizes or locations of the elements shown.

DESCRIPTION OF THE PREFERRED EMBODIMENT

Figure 1:
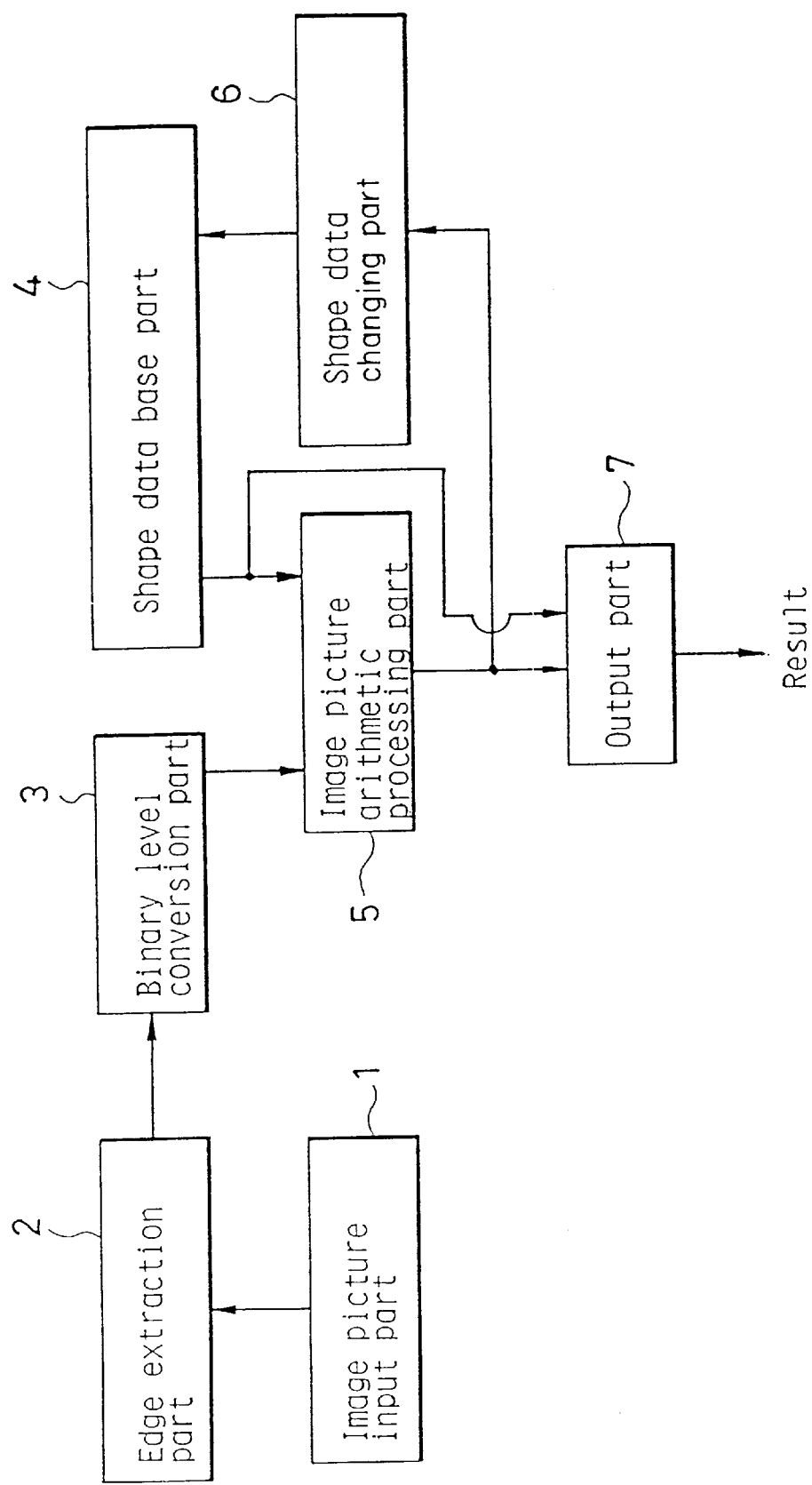
FIG. 1 is a block diagram of a first embodiment of the present invention.
Figure 2:
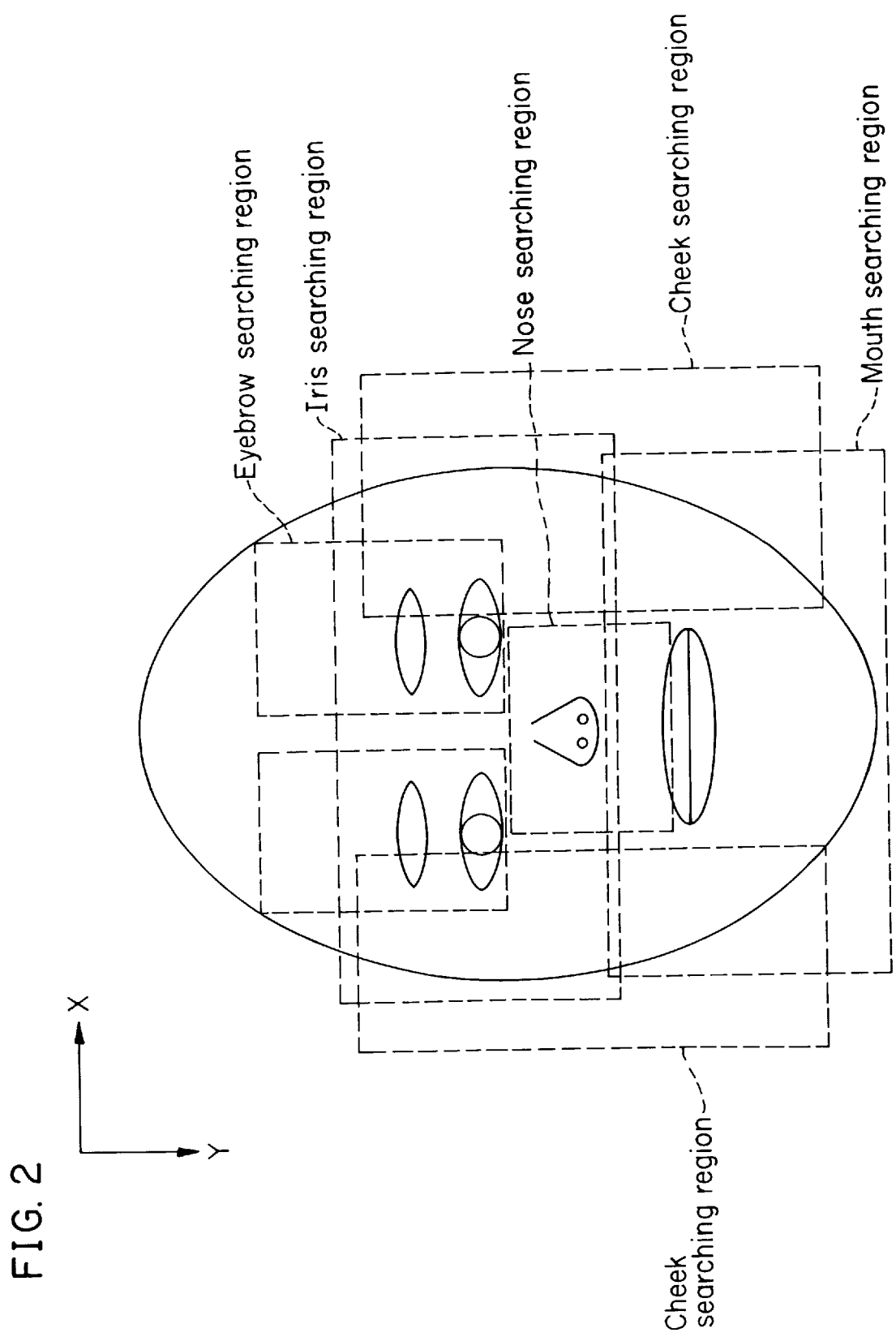
FIG. 2 shows an example of the input image picture and its searching regions.

In FIG.1, a block diagram of a first embodiment of the present invention is shown. The output of the image picture input part 1, to which facial images from a television camera or the like are input, is provided to an edge extraction part 2, wherein edge processing is applied to the input image picture. The output, on which edge processing has been applied in the edge extraction part 2, is provided to a binary level conversion part 3. A binary level conversion process is performed in the binary level conversion part 3 on the extracted edges of a searching region of the facial image. FIG. 2 shows the relationship between a face and each searching region for each facial element, namely an iris searching region for two irises, a mouth searching region for a mouth, a nose searching region for a nose, an eyebrow searching region for each eyebrow and two cheek searching regions for left and right cheeks. Each searching region is designed considerably larger than the related facial element or facial elements as shown in FIG. 2.

Several preestimated regions for each facial element are obtained. Each preestimated region is designed slightly larger than each facial element. FIG. 2(a) shows examples of preestimated regions, namely two iris preestimated regions, a mouth preestimated region, a nose preestimated region, two eye-brow preestimated regions, and two cheek preestimated regions. Each preestimated region is designed slightly, e.g., about 20%, larger than each facial element.

A shape data-base part 4 stores shape data for respective facial elements, such as the iris, mouth, nose, eyebrow, left cheek and right cheek . The binary leveled extracted edges of the facial image picture, which are processed by the binary-level conversion part 3, and the shape data copied from the shape data having been previously stored in the shape data-base part 4, are input into the image picture arithmetic processing means 5, wherein the correlation value between the copied shape data and the binarized edged image of the searching region is computed. The searching regions having high correlation values are hereafter called preestimated regions. A searching region may have a plurality of preestimated regions or no preestimated regions. Starting from the correlation values thus computed, the data copied from the contents of the shape data-base part 4 are changed by the shape data changing part 6, such that the correlation value increases in the preestimated region. Such updatings are carried out after every detection of facial element. However, in the below-mentioned example, the steps of updating are not described for all the cases.

When two iris preestimated regions are detected, for example, in one iris searching region of FIG. 2, the two preestimated regions will be the true facial element, since there are two irises on a face. However, when three or more iris preestimated regions are detected, they are determined not to be the true facial element(s) since a face has only two irises.

Let us consider a case in which preestimated regions 1, 2, 3, 4, 5 and 6, shown in FIG. 2(a), are detected as iris preestimated regions in the iris searching regions. In this case, when the preestimated region 5 (or 6) of FIG. 2(a) is examined in combination with the other preestimated regions 1, 2, 3, or 4 of FIG. 2(a), the preestimated region 5 (or 6) is not determined as the iris preestimated region because a distance and inclination between the combined preestimated regions are too different from those of stored data for iris regions.

When the preestimated region 1 or 2 is examined to determine whether it is of an iris, none of the preestimated regions 1 or 2 are determined to be an iris preestimated region, because these regions 1 or 2 fail to have a round shape portion of an iris. Hence they have a low correlation value for an iris.

When the preestimated regions 3 and 4 are examined to determine whether they are of an iris, these preestimated regions 3 and 4 are determined to be iris preestimated regions, because these regions have a round shaped portion, and they also have a high correlation value with regard to a distance therebetween and an inclination of the line connecting to the irises.

Every time after the above-mentioned respective steps are performed, the coordinates of feature points of the preestimated regions are computed. Based on the computed results of the correlation values, the shape data copied from the shape data-base part is updated. When there is at most one preestimated region included in the iris searching region, the searching region may be of in error or there may not be an image of a face being inputted. From the shape data in the shape data-base part 4, and the correction value obtained by the image picture arithmetic processing part 5, the feature points of the facial image picture are obtained and issued from the output part 7.

Concerning the mouth, one mouth searching region shown in FIG. 2 might include two or more preestimated regions. For example, when one (single) mouth preestimated region is detected so as to be included in the mouth searching region of FIG. 2, the mouth preestimated region will be the true facial element. However, when two or more preestimated regions 7 and 8 are detected, as shown in FIG. 2A, a preestimated region 7 having the highest correlation value with the mouth shape data is determined to be the true mouth.

Thereafter, similar processes are carried out for a nose, eyebrows and cheeks. Because these steps are similar to the above-mentioned ones, the details are omitted from the explanation.

The following, explanation provides more details of the procedure for extracting the feature points of a facial image.

First, the facial image picture is taken from the image picture input part 1, and the edges are extracted from the facial image picture to produce an edged image picture by the edge extraction part 2. In this part, computing is performed by using an operator, such as, for example, the Sobel operator (see, for example, p.98 of D. H. Ballard and C. M. Brown, translated by Akio Soemura "Computer Vision" Japan Computer Association, 1987), wherefrom gradient vectors of the image at respective pixels can be obtained. Copied data of the gradient vectors of the image, thus obtained, have respective magnitudes as well as directions indicative of information about the image. The direction of the gradient vector of the image indicates a direction from the point in which the brightness of the image picture has a largest value to the point which brightness is the smallest, and the magnitude thereof represents the value of the change of the brightness. Hereinafter, the gradient vectors of the image are defined to be the edge vectors, since a pixel of the edge in the image has a magnitude and direction. FIG. 2 shows an example of the input image picture and the searching regions where feature points of facial elements in a facial image are expected.

In the following, taking the iris region as an example, the procedure of extracting the iris region of a facial image from an edged image picture is described. First, the magnitudes m of edge vectors in the iris searching region shown in FIG.2 are converted into binary-leveled values of 0 or 1 using a certain threshold value θ. That is, the raw edge vectors obtained by applying an edge extraction operator, such as the Sobel operator described above, on the brightness data of respective pixels (or positions), are normalized and converted into either unit vectors or zero vectors. Hereinafter, for the convenience of explanation, the sign of these unit vectors obtained, as has been described above, is reversed (multiplied by −1), and they should be called normalized edge vectors. This process is carried out in the binary level conversion part 3. Since the magnitudes m of edge vectors vary depending on the lighting conditions used when taking the facial image picture, the above-mentioned threshold value θ is determined to be within a region including only 20% of the largest magnitude as determined from a frequency distribution of the magnitude m. For example, the threshold value θ is determined in a manner such that the binary level conversion is made by setting those data, which fall within the top 20% largest probability of distribution of the largest magnitude in a relevant searching region, to 1, whereas the rest of the data falling within the outlying 80% probability region of smaller magnitude vectors are set to 0.

Figure 4:
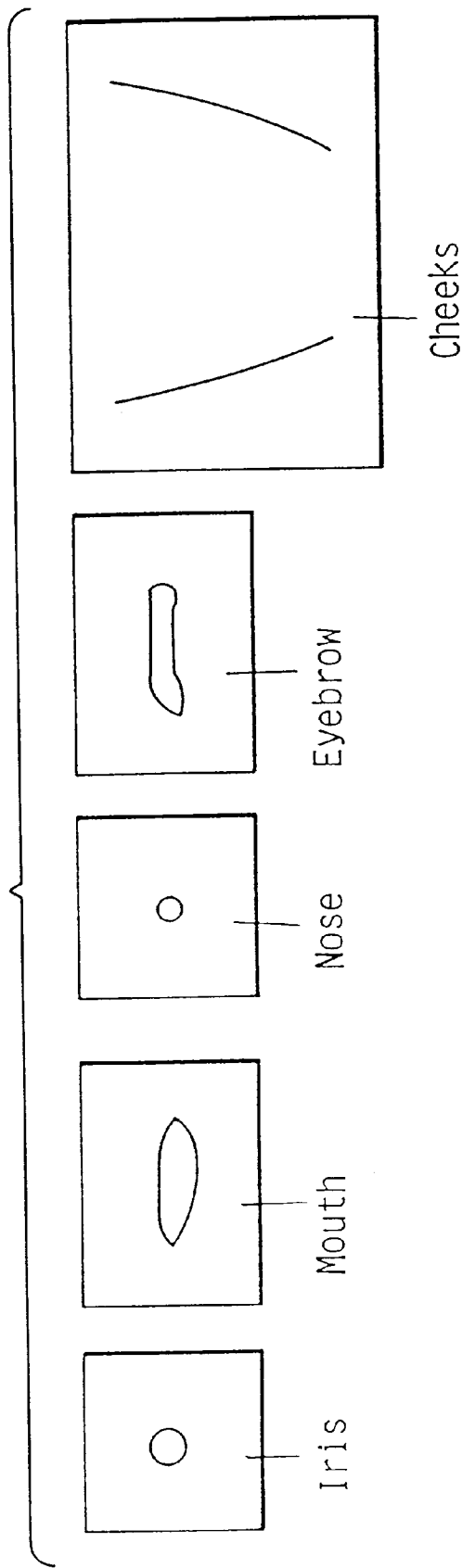
FIG. 4 shows an example of shapes of respective facial elements.

In FIG. 3 and FIG. 4, an example of the contents stored in the shape data-base part 4 is shown. FIG. 3 shows shape data of an iris, as an example. In this case, the number n of positions of the shape data is twelve, that is, n=12. The shape data comprise twelve coordinate data and twelve gradient vectors at those respective coordinates. Coordinate data, ($l_k$, $m_k$) are coordinates at which gradient vectors, ($v_x$, $v_y$) are given. The gradient vectors ($v_x$, $v_y$) are unit vectors giving the direction in which the largest gradient value is present. Since the iris has a circular having a much darker inside than an outside thereof, coordinate data form a circle and all the gradient vectors given at these coordinates are multiplied by (−1) so as to be directed toward the center of the circle.

FIG.4 shows examples of facial elements and their shapes. The facial elements are an iris, a mouth, a nose, an eyebrow, and a cheek, in this embodiment.

Next, the searching region for the edged image picture of the iris is scanned and the correlation value φ between the edge vectors of the input facial image picture and the gradient vectors of the shape data stored in the data-base is calculated in the arithmetic processing part 5. Since both the edge vectors of the input facial image picture and the shape data stored in the data-base part 4 are given in the form of a vector, the correlation value φ can be expressed by the average of inner products between those corresponding two vectors in a manner shown below.

Letting the edge vectors of the input facial image picture be $$u_{i,j}=(u_x, u_y)$$

where i, j are x, y coordinates of positions on the image picture and the magnitude of the edge vectors be binarized (normalized) to 1 or 0:

$$u_x^2 + u_y^2 = 1, \text{ or } 0$$

and the shape data is coordinate data: $P_k=(l_k, m_k)$ where $l_k$, $m_k$ are x, y coordinates of positions of the shape data, respectively, and gradient vectors: $v_k=(v_x, v_y)$ such that $v_x^2+v_y^2=1$ and $1 \geq k \geq n$ (n is number of the positions), then the correlation value φ of the shape data at coordinates (i,j) in the image picture is defined as $$\phi = (\Sigma u_{i+l_k, j+m_k} \cdot v_k)/n,$$

where $1 \geq k \geq n$ and $$u_{i+l_k, j+m_k} \cdot v_k = u_x \cdot v_x + u_y \cdot v_y.$$

In a manner described above and by scanning the coordinates (i,j), the correlation value factor φ for respective coordinates (i,j) in the searching region are calculated. A region including those coordinates having a largest correlation value φ is assigned to be the preestimated of the relevant facial element.

Next, in respective preestimated regions, the copy of the shape data are changed by the shape data changing part 6, and then the correlation value φ is again searched. The scheme of changing is, for example, to move the coordinate of one position of the present data by +1 and then by −1 in the direction of the gradient vector and to change the data in the direction in which the correlation value increases. After this movement, the direction of the gradient vector of the position is also changed in a manner such that it coincides with the shape data. In such a manner, all of the elements of the stored shape data are successively changed in a manner that further improves the correlation value φ. When the improvement of the correlation value φ stops, or when φ exceeds a certain specified value s, any further changing of the copy of the shape data is stopped.

Thereafter, in accordance with the updated shape data, the feature points of a facial image are issued from the output part 7. The scheme of this outputting is as follows: for example, when a final value of the correlation value φ is less than a certain value t (s>t), the region having the maximum correlation value φ is taken as the preestimated region. The shape data in that region represents a facial element to seek, however, only the necessary feature points of a facial image are obtained. And when there are a plurality of preestimated regions in which the correlation value φ is larger than a certain value t, the preestimated region is determined by, for example, a statistical procedure. That is, those regions which are disposed mutually close are all regarded to be genuine shape data. By calculating an average with regard to corresponding positions of all of these shape data, new shape data are obtained.

Then, taking the obtained shape data to be the shape data of a facial element, namely the object to search for, only the necessary feature points of a facial image are output. For example, in the case of the iris, the average of the coordinates of all the positions of the shape data are calculated to be a center point, and the maximum point and minimum point in the y-coordinate are taken to be the top and the bottom points of the iris. Resultant data are then issued from the output part 7.

Hereupon, since two irises are present in the x-coordinate direction on a face, it is necessary to issue two positions, separated by at least a distance d at which the correlation value φ is large, to be the two irises.

In a similar manner, the respective feature points of the mouth, nose, eyebrow, and cheek can be extracted from a facial image. For example, for the mouth, five points being the top, bottom, left, right, and center are extracted; and for the eyebrow, four points being the top, bottom, left, and right are extracted.

Figure 5:
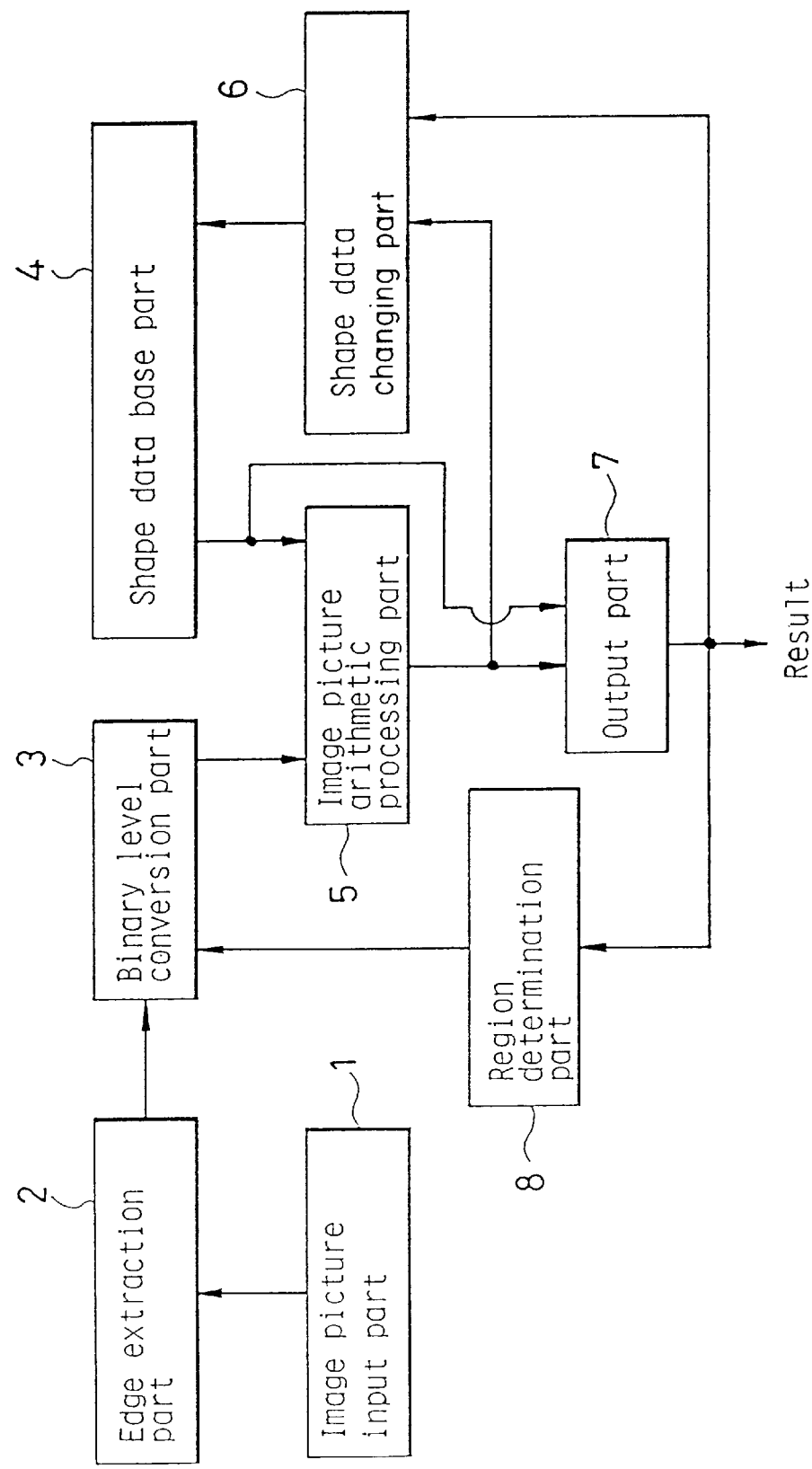
FIG.5 is a block diagram of one embodiment of the present invention.

FIG. 5 shows a block diagram of a second embodiment. FIG. 2 describes searching only the iris region, for example. The searching regions for remaining facial elements are determined by the region determination part 8 based on the extracted feature points of the irises. In accordance with such a process, it becomes possible to extract the feature points for remaining facial elements with fewer calculations. For example, the determination of the searching regions for the remaining facial elements can be processed by utilizing simple common knowledge, such as that the nose is present between mouth and eyes, and the eyebrows are present immediately above the eyes.

Furthermore, once the coordinates of two irises are determined, any possible tilt angle of the input facial image picture can be obtained. Hence, based on the tilt angle, the copy of the shape data stored in the shape data-base 4, is rotated 4 by an amount of the obtained tilt angle by the shape data changing part 6. Thus, even from a tilted facial image picture, the extraction of the feature points becomes possible.

Figure 6:
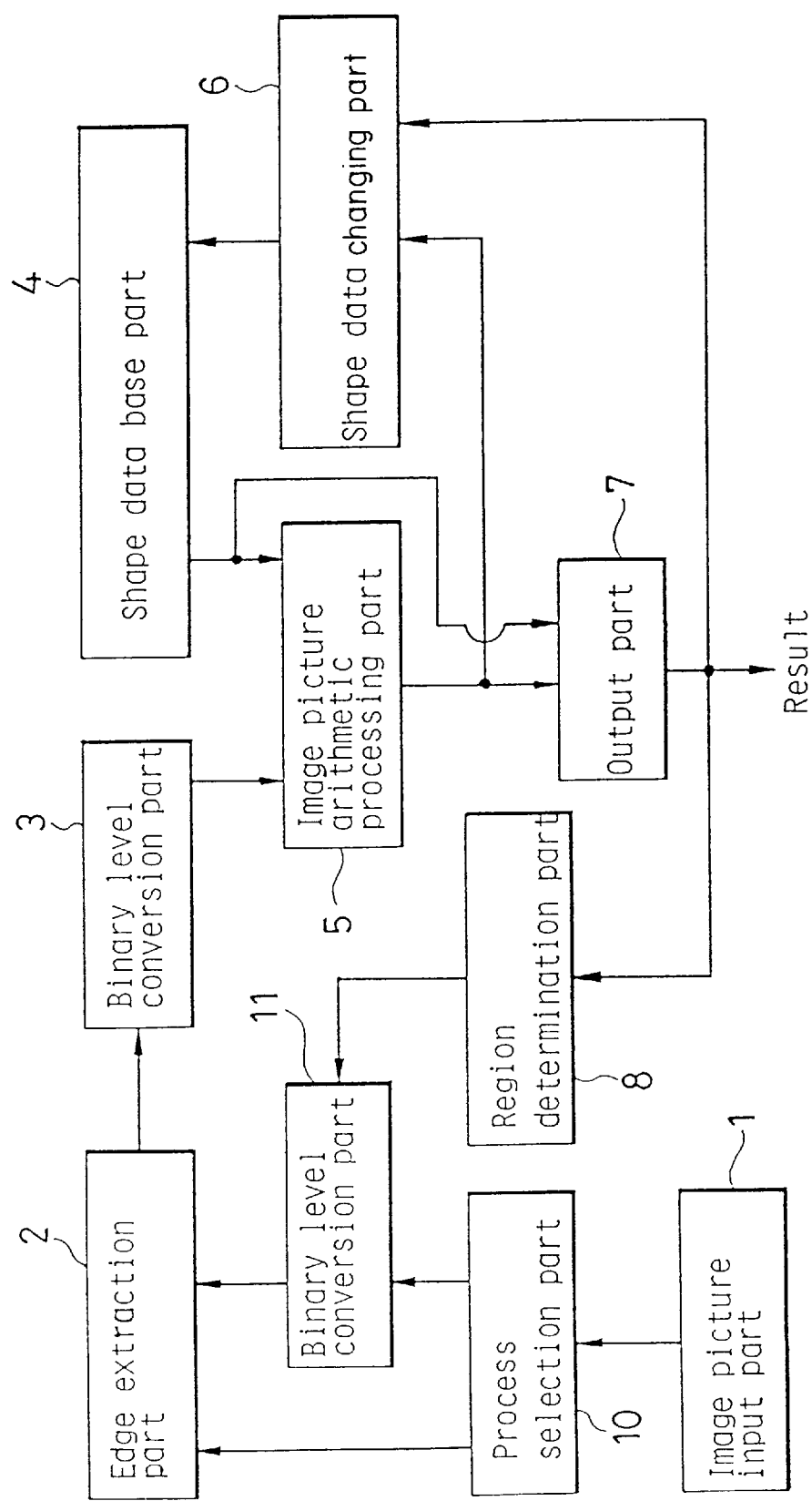
FIG. 6 is a block diagram of another embodiment of the present invention.

FIG. 6 shows a block diagram of a third embodiment of the present invention. The eyebrow has an edge which is not sharp but gradual. This is because the borders of hair of the eyebrow are gradual. Therefore, the eyebrow differs from the other facial elements in that it is difficult to obtain strong edge components. Consequently, for the extraction of the feature points of the eyebrow, by applying a preprocessing of binary level conversion on the searching regions of eyebrows by a binary level conversion part 11, it becomes possible to obtain strong edge components. This preprocessing is selected by the process selection part 10.

The application of the above-mentioned capability of the present invention is not limited to the eyebrow, but it is also valid, for example, to features such as the moustache wherein its edge component is also gradual. In particular, in the case of extracting the feature points of the eyebrow, since the eyebrow is horizontally oblong, its brightness distribution differs largely between both ends. Consequently, if the searching region is binary-leveled only one time, an accurate shape of the eyebrow may not appear. Then, (as in the aspect described in claim 5) the searching region of the eyebrow is divided into small sub-regions in the vertical direction. In respective small sub-regions, respective threshold values for binary level conversion are respectively determined in a manner such that j % probabilities of brightness distribution is set to 0. Hereupon, j is determined in accordance with, for example, the area of respective searching regions. By obtaining the average and variance of the threshold values for respective small sub-regions, respective regions can be binary-leveled individually. During this process, when the threshold value deviates largely from the average value, it is regarded that either (i) There is no eyebrow in that small subregion, or (ii) There is a lot of hair.

Thus, the process is carried out on respective small subregions by which the whole parts of those small subregions are binary-leveled totally to 0 or 1 in accordance with the above classifications.

The present embodiment is valid not only for a situation such that the lighting source deviates from the center of the face to the right or left direction, but also such in that the influence of hair existing in the eyebrow region can be reduced.

Figure 7:
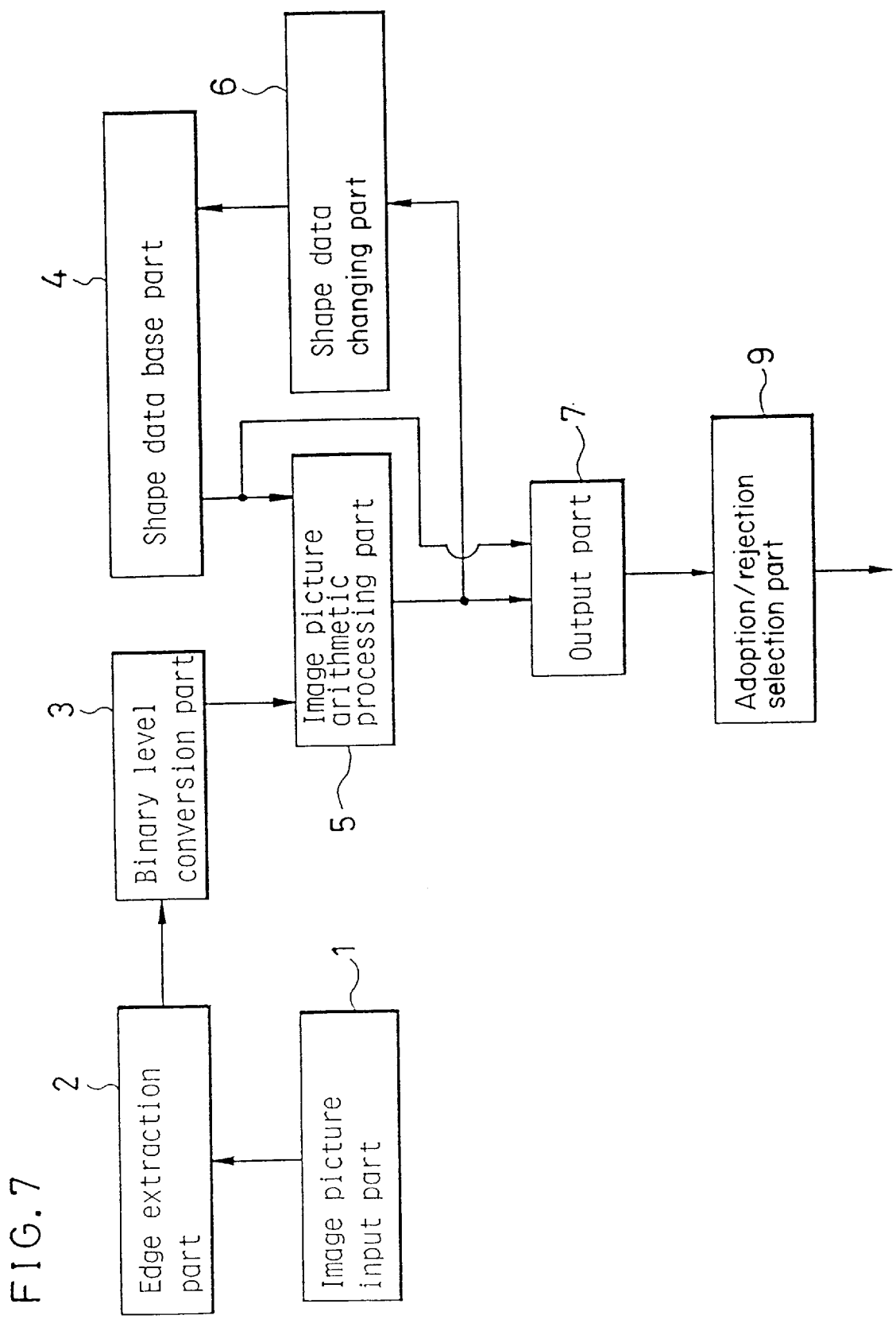
FIG. 7 is a block diagram of yet another embodiment of the present invention.

In FIG. 7, a block diagram of a fourth embodiment of the present invention is shown. In the case of the present embodiment, the searching regions obtained for respective facial elements are recorded in the adoption/rejection selection part 9; and from the combination thereof, one giving an adequate facial shape is selected. As the condition to obtain an adequate facial shape, the following facts, for example, can be used:

(iii) A nose and mouth are present on an equidivision perpendicular line between two irises, (iv) A distance between two eyebrows and between two irises are almost the same, and (v) The right cheek and the left cheek are present at almost equidistant places to the right hand side and the left hand side from the above equidivision-perpendicular line.

In such a manner, the best fit searching regions are searched for respective facial elements. Then for respective searching regions, the feature points of facial elements which are the object of a search can be obtained based on the shape data.

In the above-mentioned example, four different embodiments of the present invention have been explained. Such embodiments may comprise hardware as shown in the Figures, but may alternately comprise a data processor. In order to elucidate the present invention embodied by using the data processor or a computer specifically and concretely, an example of a hardware configuration of a computer for use in the present invention is shown in FIG. 8, and an example of the procedure of extraction of the feature points of facial elements, which has been already described in the above embodiments, is now explained using the flow chart shown in FIG. 9(*a*) and FIG. 9(*b*).

Figure 8:
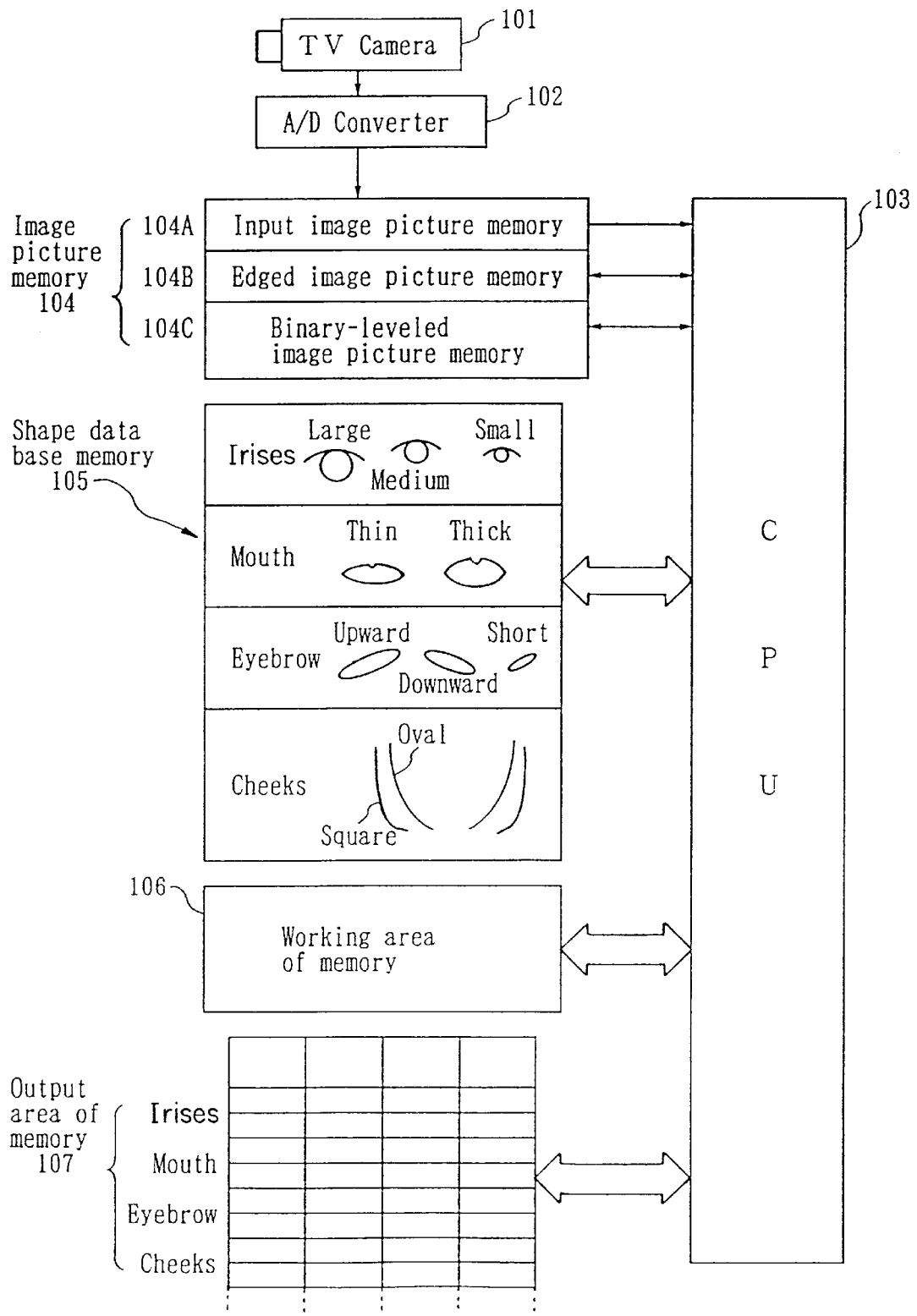
FIG. 8 shows an example of a hardware configuration of the present invention.

FIG. 8 shows a circuit block diagram giving a fundamental hardware configuration of the apparatus of the present invention. The facial image picture is input to the apparatus through a television camera 101. The facial image picture signal issued from the television camera 101 is input into an A/D converter 102. A central processing unit, CPU 103, executes all the required functions, such as data access, data transfer, data storage, arithmetic processing, and other functions for data under instructions from the program installed in the apparatus. The functions or parts represented by boxes in FIG. 5 through FIG. 7 are preferably executed by such an installed program. Numeral 104 designates an image picture memory. The output of the A/D converter 102 is memorized through the CPU 103 in an input image picture memory 104A as the input image picture data for all pixels. The input image picture data are converted into an edged image picture data by extracting the edges of the same and further-converted to binary-leveled edged image picture data by the CPU 103. They are stored in an edged image picture memory 104B and a binary-leveled edged image picture memory 104C, respectively. Numeral 105 is a memory for storing the shape data-base of facial elements such an iris, a mouth, an eyebrow, or a cheek. The data-base of each facial element includes three different sizes—small, medium and large. The correlation value between the binary-leveled edged image picture data and a copy of the copy of the shape data stored in the shape data-base memory 105 is computed; and the copy of the shape data are changed by the CPU 103 in a manner such that the correlation value increases. Numeral 106 is a working area of memory temporarily used for processing. Numeral 107 is an output area of memory for storing the extracted feature points of the necessary facial elements.

Figure 9B:
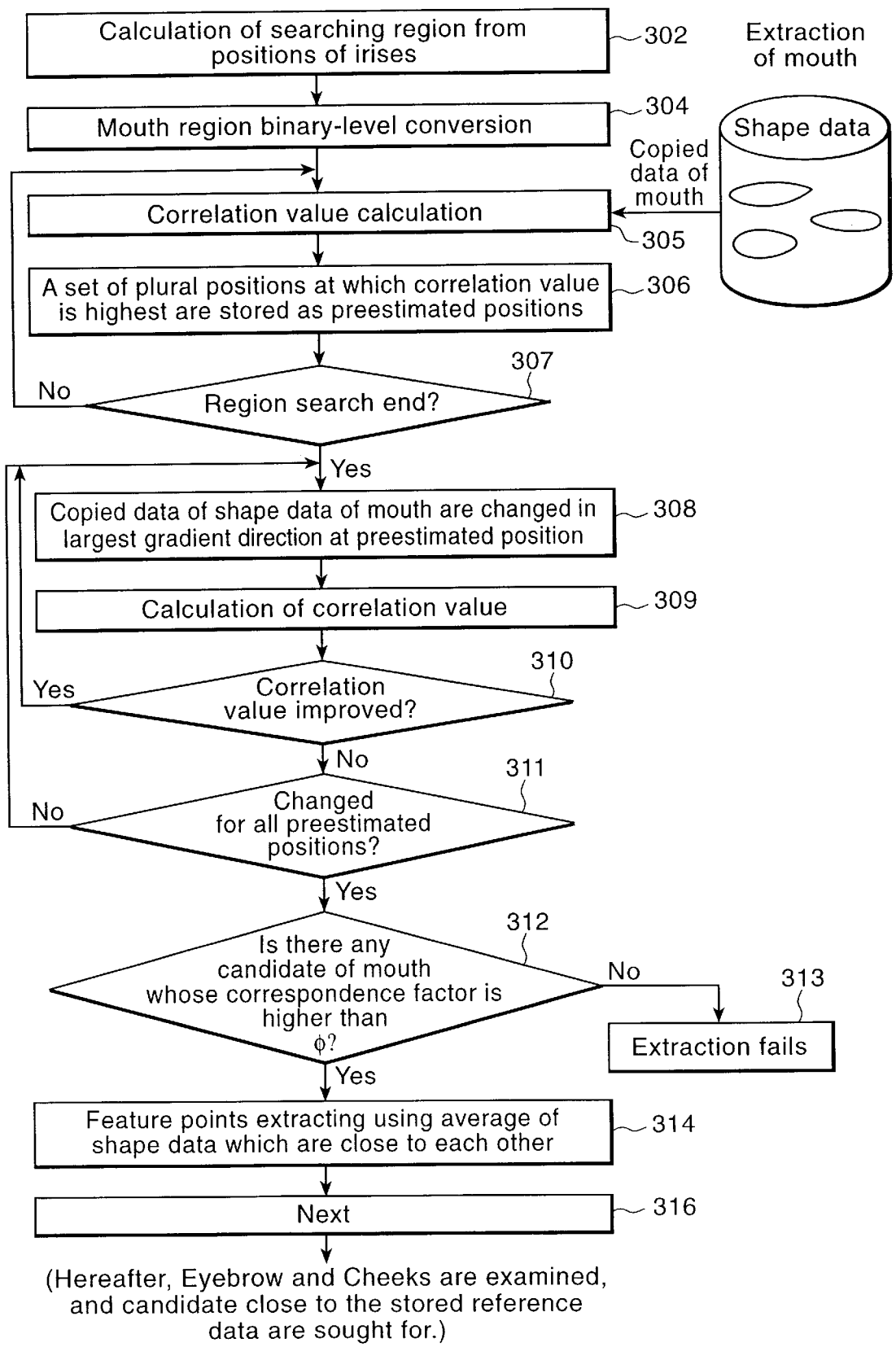

In FIG. 9(a) and FIG. 9(b) in combination, a flow chart of an example of the procedure of extraction of the feature points is shown. In FIG. 9(a) a flow starting at a start 201 through a step 216 corresponds to the process for the extraction of feature points of the iris, whereas in FIG. 9(b), a flow of step 302 through step 316 corresponds to the process for the extraction of feature points of the mouth. For other remaining facial elements, almost the same flow chart as for the above two facial elements can be applied.

Hereupon, in the present invention it is unnecessary to use any color picture image, and thereby the extraction of the feature points of a face is possible even from a monochromatic photograph. For the shape data, by preparing a plurality of data for each facial element, the obtainable accuracy of extraction of the feature points can be improved.

Although the present invention has been described in terms of the presently preferred embodiments, it is to be understood that such disclosure is not to be interpreted as limiting. Various alterations and modifications will no doubt become apparent to those skilled in the art after having read the above disclosure. Accordingly, it is intended that the appended claims be interpreted as covering all alterations and modifications as fall within the true spirit and scope of the invention.

We claim:

1. An apparatus for outputting data indicative of matching features of a face with data in a data-base, said apparatus comprising:

an image picture inputter for receiving an input image of a face, said image including a plurality of facial feature searching regions each of which corresponds to a respective facial feature of said face;

an edge extractor for processing said input image of said face to form an edged-image of said face;

a binary level converter for dividing said image into said plurality of facial feature searching regions and subsequently performing a binary level conversion on said edged-image of said face corresponding to a plurality of facial feature points of said face, said binary level converter converting said edged-image of said face into a binary-leveled edged-image of said face;

a shape data-base permanently storing a plurality of shape data as a reference data-base for said plurality of facial feature points, said shape data comprising coordinate data and gradient vectors in x,y coordinates;

an image picture arithmetic processor for determining an amount of correspondence by computing a correlation value between data of each of said plurality of facial feature points of said binary-leveled edged-image of said face and each corresponding one of said plurality of facial feature points of said shape data stored in said shape data-base;

a shape data-base changer for changing copied data of said plurality of shape data copied from said shape data-base; and an outputter for outputting data indicative of said matching features of said face based on said correlation value and said copied data, wherein using both said edge extractor and said binary level converter results in decreased sensitivity of said apparatus to changes in lighting.

2. An apparatus in accordance with claim 1, said apparatus further comprising:

a facial feature region determiner for determining locations of others of said plurality of facial feature searching regions based on said data output from said outputter with respect to a determination of a first facial feature.

3. An apparatus in accordance with claim 2, wherein:

a region of irises of said face is determined before said facial feature region determiner determines said locations of said others of said plurality of facial feature searching regions.

4. An apparatus in accordance with claim 2, further comprising a second binary level converter arranged to perform binary level conversion before said processing of said input image of said face by said edge extractor.

5. An apparatus in accordance with claim 4, when said:

second binary level converter is connected to said edge extractor and is arranged to receive an output of said facial feature region determiner, to divide one of said plurality of facial feature searching regions into a plurality of smaller sub-regions, and to determine a binary level conversion threshold value for each of said plurality of smaller sub-regions from a brightness distribution of each of said plurality of smaller sub-regions.

6. Amended) An apparatus in accordance with claim 1, said apparatus further comprising:

an adoption/rejection selector for obtaining expected positions of said plurality of facial features, which obtains and determines an accuracy of positions of said plurality of facial features, and which discards any erroneously extracted facial features prior to processing said input image of said face by said edge extractor.

7. An apparatus in accordance with claim 1, wherein:

said edge extractor includes a computer using a Sobel operator which produces gradient vectors for respective pixels of said image of said face, said gradient vectors having magnitudes and directions indicative of said facial features.

8. An apparatus in accordance with claim 1, wherein:

an arithmetic computation performed by said image picture arithmetic processor is an inner product between compared gradient vectors of said binary-leveled edged-image of said face and respective shape data.

9. An apparatus in accordance with claim 8, wherein:

a location of at least one of said plurality of facial feature searching regions is determined by a location on said image of said face where said correlation value is largest.

10. An apparatus in accordance with claim 3, wherein:

said respective locations of said others of said plurality of facial feature searching regions are determined with reference to a position of said region of said irises of said face.

11. An apparatus in accordance with claim 1 wherein said shape data-base changer changes said copied data by a method comprising:

(1) displacing said coordinate data by ±1 in a direction of said gradient vector, (2) changing said direction of said gradient vector after said step of displacing said coordinate data, so as to match said shape data at said displaced coordinate data, (3) repeating steps (1) and (2) by displacing said coordinate data further by ±1 thereby pursuing an increase in value of said correlation value, and (4) ceasing said repeating step when one of said value of said correlation value no longer increases and said value of said correlation value exceeds a predetermined threshold value.

12. An apparatus in accordance with claim 1, wherein said shape data comprises:

said coordinate data which are defined as: $P_k=(l_k, m_k)$, where $l_k$, $m_k$, are x, y coordinates of a k-th position at which said shape data is given, respectively, and said gradient vectors are defined as: $v_k=(v_x, v_y)$, where $v_x^2+v_y^2=1$ and
$1 \leq k \leq n$ (where n is a number of positions).

13. An apparatus in accordance with claim 2, wherein said shape data comprises:

said coordinate data which are defined as: $P_k=(l_k, m_k)$, where $l_k$, $m_k$, are x, y coordinates of a k-th position at which said shape data is given, respectively, and said gradient vectors are defined as: $v_k=(v_x, v_y)$, where $v_x^2+v_y^2=1$ and
$1 \leq k \leq n$ (where n is a number of positions).

* * * * *